United States Patent [19]

Kniker

[11] 3,969,497

[45] July 13, 1976

[54] TEST SUBSTANCE FOR TUBERCULOSIS

[75] Inventor: William T. Kniker, San Antonio, Tex.

[73] Assignee: Lincoln Laboratories, Inc., Decatur, Ill.

[22] Filed: May 5, 1971

[21] Appl. No.: 140,444

[52] U.S. Cl. ................................................. 424/12
[51] Int. Cl.[2] ......................................... A61K 39/00
[58] Field of Search .................................. 424/12, 8

[56] References Cited
UNITED STATES PATENTS

| | | | |
|---|---|---|---|
| 2,204,272 | 6/1940 | Gruskin | 424/12 |
| 2,901,398 | 8/1959 | Perlman | 424/12 |
| 3,105,012 | 9/1963 | Brandon et al. | 424/12 |

FOREIGN PATENTS OR APPLICATIONS

| 487,199 | 12/1929 | Germany | 424/12 |
|---|---|---|---|

Primary Examiner—Frederick E. Waddell
Attorney, Agent, or Firm—Norman Lettvin

[57] ABSTRACT

A new test substance for use in skin testing for tuberculosis, which substance is produced from *Mycobacterium tuberculosis* (*M.tb.*) culture filtrate or bacillary extract. The culture filtrate or extract is first fractionated by means of chromatography. Resultant fractions are then further fractionated so as to produce subfractions which contain at least one *M.tb.* specific antigen and are substantially free of antigens crossreactive with atypical mycobacteria. At least two of these subfractions may then be combined to produce a mix or new test substance, containing a plurality of *M.tb.* specific antigens only, capable of stimulating lymphocytes in individuals previously sensitized to *M. tuberculosis* antigens.

8 Claims, 7 Drawing Figures

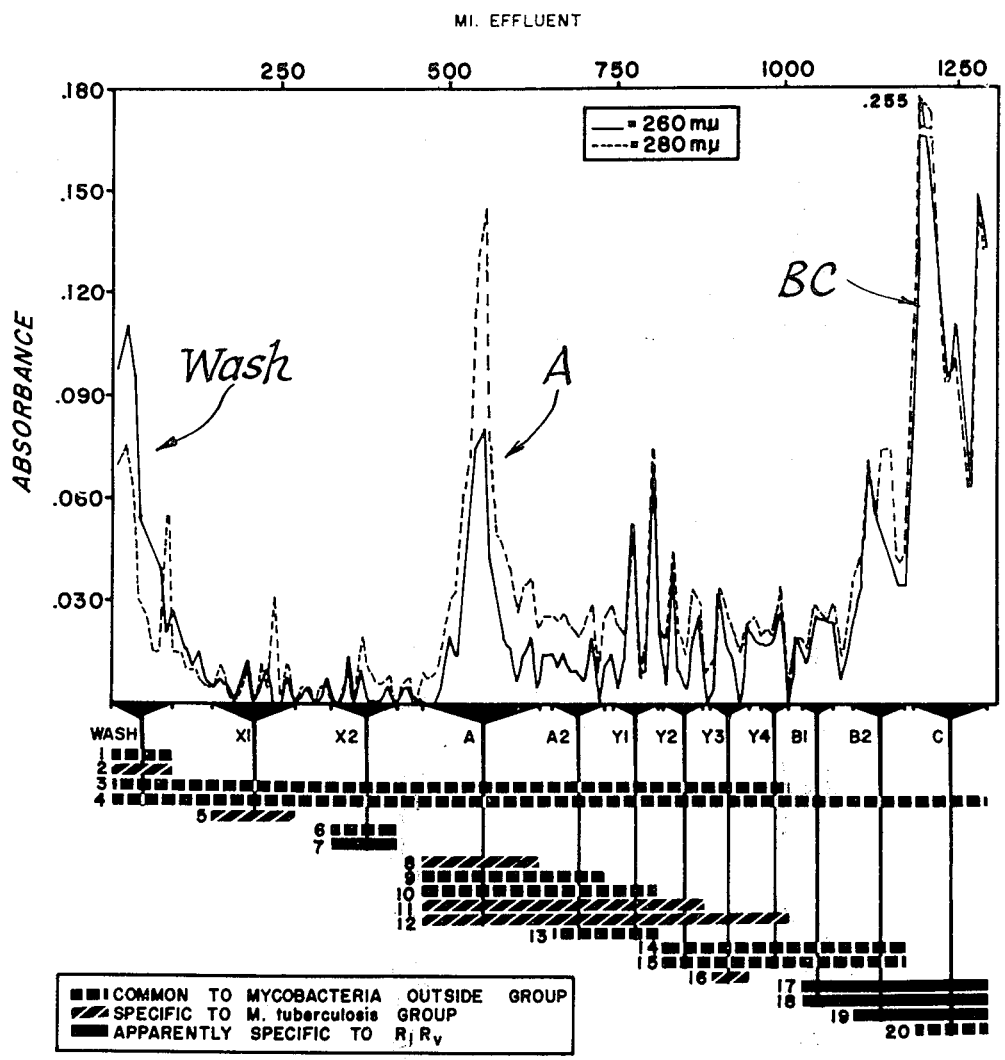

TEST SUBSTANCE FOR TUBERCULOSIS

BACKGROUND OF THE INVENTION

This invention relates to an improved antigenic substance for testing for tuberculosis and to the method for preparing such antigenic substance.

It has been known for many years that exposure of a human being to the disease commonly known as tuberculosis, resulting from an infection by *Mycobacterium tuberculosis* (*M. tb.*) may be tested for by an intradermal injection of antigenic material derived from tubercle bacilli or their products. The antigenic material, tuberculin, induces sensitized lymphocytes to initiate a delayed hypersensitivity response at the site of the injection. The subsequent swelling at that site is known as edema or induration, and the reddening in the area is known as erythema. After a selected lapse of time, generally 48 to 72 hours, the size of the edematous swelling is measured and compared to previously established statistical standards that relate size of reaction after a particular dose of antigen to probability and recentness of prior infection with *M. tb.* Thus, an evaluation is made as to whether the injectee is a "positive" or "negative" reactor.

A number of antigenic materials or tuberculins exist or have been suggested, and a number of intradermal injectors have been used. The classical standard of injector is a needle and syringe using a technique known throughout medical literature as the "Mantoux test", a technique that requires considerable skill both in administration and in evaluating the results. Other injectors and techniques include and have included a simple scratch test, the "Vollmer" patch test, multiple scratch scarifications by an instrument known as the Heaf gun (also known by the Trademark "Sterneedle"), or by simultaneous skin puncture and injection as effected by instruments known as "Mono-Vacc" of Lincoln Laboratories and "Tine Test" of Lederle Laboratories. For reasons that are unimportant here, the Mantoux test is generally accepted as a standard diagnostic test while use of the other instruments is generally considered a "screening" test useful as a first test in screening from a large group of humans being tested, those who appear to be clearly positive reactors. Some of the test noted, such as the Vollmer patch test, have been discarded as unreliable.

The problem of "unreliability" is constantly present as a factor even with use of the Mantoux test. A major reason for the unreliability factor stems from the nature of the antigenic material used by the test instruments and test techniques. Until now the two tuberculins used are known in the medical literature as "Old Tuberculin" (OT) and "Purified Protein Derivative" (PPD), a derivative of OT.

The medical literature has for years noted the existence of the unreliability factor under the term "false positives" with respect to use of OT and PPD. These undesirable reactions stem principally from stimulation of lymphocytes previously sensitized by prior exposure or infection by other bacteria, such as "atypical mycobacteria" which are closely related to *M. tb.* Certain antigens are shared in common by *M. tb.* and the other mycobacteria. If these shared or "cross-reactive antigens" are present in the tuberculin injected into the skin, an individual previously infected by mycobacteria other than *M. tb.* could give a positive response.

The existence of false positives resulting from use of OT or PPD with all types of injectors or scratch instruments has created a real problem of long standing duration to the medical community. It has been widely acknowledged that a specific antigenic material, that may be used in a reliable and efficient manner as a diagnostic test for *M. tb.*, is greatly needed.

It has been a postulate of some researchers in the field that isolation of a single antigen specific to *M. tb.* would provide the ideal antigenic material for diagnostic skin testing for *M. tb.*, and for diagnostic tests of *M. tb.* sensitization or infection, in vitro.

Many studies have been made of the antigenic "mix" of *M. tb.* culture filtrates toward the end of somehow selecting and isolating an antigen of diagnostic reliability and great specificity; many techniques have been devised for such mycobacterial antigen isolation. See, for example, *American Review of Respiratory Diseases*, Vol. 89, No. 1, January, 1964 P. 29 et seq. and Vol. 92, December, Part 2, 1965, P. 19 et seq. However, until now, it appears that the key to preparation of an antigenic material that has both high specificity and high sensitivity has eluded the search by investigators, despite the fact that antigens specific for *M. tb.* appear to exist and the literature describing preparative and analytical methods for the separation and isolation of antigens of *M. tb.* has been available for many years.

SUMMARY OF THE INVENTION

A single isolated antigen of *M. tb.*, even if highly specific for *M. tb.* strains is unlikely to provide a satisfactory tuberculin for widespread use in diagnostic testing for number of reasons. In *M. tb.* sensitized humans and animals prohibitively large doses of a single antigen are required to obtain even weak positive delayed hypersensitivity reactions in a small proportion of individuals. It is theorized that single antigens cannot elicit a response from a sufficient number of lymphocytes to initiate a sufficient inflammation. For this reason undesirable immediate hypersensitivity reaction in the skin mediated by antibodies or immunization of the tested individuals to large dose of antigen could occur. Furthermore, it is possible that some individuals or animals will not develop immunity or immune responses to particular antigen; this can be on a congenital or acquired basis. A particular single antigen may not be found in all *M. tb.* strains capable of infecting an individual or animal; and if this antigen was not present in an organism which infected even a small quantity of individuals or animals, the diagnostic utility and reliability of that single antigen would be seriously impaired.

The physicochemical character of a single antigen may, in certain individuals, not elicit the desired positive delayed hypersensitivity response in vivo or in vitro; one such *M. tb.* antigen may be one that is predominantly carbohydrate. It has also been shown that prior infection or sensitization by certain atypical mycobacteria cause the hypersensitivity response to single antigen to disappear, even when the tested individual or animal had more recently been infected and sensitized by *M. tb.* organisms.

Indeed it has been discovered that a mix of multiple antigens specific for *M. tb.*, which exhibit separate and distinct physical and chemical characteristics as detected by chromatographic and other separation techniques, will synergestically increase the delayed hypersensitivity response without a decrease in specificity.

The use of such a mixture of specific antigens leads to a response of desirable specificity, at much lower dosages than necessary when only a single *M. tb.* antigen is used.

Thus, a new antigenic test substance is provided which is substantially free of cross-reactive antigens and which thereby assures a positive delayed hypersensitivity response to an intradermal injection of reasonable antigenic quantity or mass so as to reliably reflect the individuals sensitization to *M. tb.* antigens only.

BRIEF DESCRIPTION OF THE DRAWING

The drawing is a graphical representation of results of spectrophotometric and immunodiffusion tests and indicates the character of various antigens which are contained in a representative *M. tb.* cultural filtrate.

DESCRIPTION OF THE PREFERRED EMBODIMENT

Before entering into a specific discussion of the process for producing the new test substance of this invention a brief overview will be beneficial. The broad steps of the method are:

I. preparing an *M. tb.* culture filtrate or bacillary extract;
II. fractionating said culture filtrate or bacillary extract and identifying the antigens in said fractions; and
III. preparing a test substance by combining a plurality of fractions which contain *M. tb.* specific antigens and are substantially free of cross-reactive antigens.

1. Preparation of Culture Filtrate

Several different *M. tb.* organisms have been used to prepare necessary *M. tb.* culture filtrates. These organisms are readily available from laboratories in the United States and may be identified as follows: C-3; C-27; H37 Rv; and TMC-107. The H37 Rv (and TMC-107 cultures were characterized as virulent and were provided by Dr. William Steencken, Saranac Lake, New York; the C-27 and C-3 cultures were obtained from Dr. J. Bates, Veterans' Administration Hospital, Little Rock, Ark. A series of atypical mycobacterial cultures were obtained from Dr. Ernest Runyon, Salt Lake City, Utah, or the Veterans' Administration Hospital in Little Rock, Ark., for use in the cross-reactive determinations and preparation of antisera. The original cultures and sub-cultures were stored on a Lowenstein-Jensen slants at 4°C. For the preparation of crude antigens, a modified Proskauer-Beck liquid medium was used. (For a further discussion of this medium, see the *Journal of Bacteriology*, 1946, Vol. 51, p. 703). After the appropriate treatment, the mediums were inoculated with each of the study organisms. After incubation the contents of the flasks were equally divided to inoculate 8 to 10 sterilized Roux bottles, each containing 250 ml. of Proskauer-Beck medium. These were then incubated for 8 to 12 weeks.

After heavy growth had occurred, the cultures were harvested and sterilized by filtration through Seitz filter pads. Most of the sterile culture filtrate was then concentrated 50 fold by vacuum dialysis; thiomerosal in the ratio of 1:10,000 was added and the mixture was then stored at −20°C until needed.

II. Antigen Separation and Identification

The next step is to fractionate the filtrate so as to separate the antigens. This can be accomplished in a number of ways. One such separation can be by ion-exchange chromatography. By so doing, a number of fractions of the filtrate can be produced some of which have been found to contain both *M. tb.* specific and cross-reactive antigens. Thus, the fractions need to be further separated or sub-fractionated.

As an alternative to chromatographic separation, electrophoretic separation may be used. It has been found by others, that the slowest electrophoretic fraction (called the A fraction) contained a large number of *M. tb.* specific antigens; a faster migrating fraction (the B fraction) contained other of the specific antigens; while the fastest moving fraction (the C fraction) contained many more cross-reactive antigens than specific ones. These named electrophoretic fractions roughly correspond in antigenic content to those chromatographic fractions designated with the same letter symbol hereinafter.

In any event, each of the major fractions whether separated by ion-exchange chromatography or electrophoresis still contains a mixture of *M. tb.* specific and cross-reactive antigens which requires further separation or sub-fractionation. This further separation or sub-fractionation can be accomplished by any one of the following processes; molecular exclusion chromatography; isoelectric focusing; or disc gel (or polyacrylamide gel) electrophoresis, particularly its "discontinuous" gel modification. By using these techniques the various antigens may be separated.

Immunodiffusion procedures can be used to determine which antigens, in any fraction or subfraction, are cross-reactive and which are specific for *M. tb.* The immunodiffusion technique utilizes hyperimmune antisera to each of many strains of *M. tb.* as well as to representative strains of the atypical groups of mycobacteria. Once the cross-reactive antigens are recognized, the fractions or subfractions containing the *M. tb.* specific antigens only are combined to form the new test substance.

To further explain the techniques used herein, a discussion of specific separation techniques and comparative techniques will be presented hereinafter as applied to various ion-exchange chromatographic fractions. It will be appreciated that the procedures useful with one fraction may also be employed with regard to the other fractions. At the present time, it is believed that the combined use of ion-exchange chromatography and some form of polyacrylamide gel electrophoresis is the most effective process.

For example, a culture filtrate produced from a strain of *M. tb.* is fractionated on a DEAE cellulose an ion-exchange column. The basic techniques used are set out in detail in the previously cited papers, and have been modified but little since. After preparing the column it is charged with the concentrated filtrate. The column is then "washed" with the initial buffer to completely elute the loosely bonded antigens. In a more recent modification, at least 500 ml. of initial buffer is used to completely elute the loosely bonded antigens to prevent their contamination of subsequent fractions. The fraction thus produced is called the "Wash Fraction", and is so indicated on the representative illustration. The initial buffer consisted of 0.01 M $Na_2 HPO_4$ adjusted to a pH of 8.0. Further elution was continued using a polystaltic pump and a Varigrad system of buffer chamber to increase the buffer molarity to as high as 0.5 molar by means of a shallow, linear gradient. As the elute came off the column it was collected in a series of tubes.

Each of the tubes were analyzed spectro-photometrically at 280 mu. to determine the presence of protein. Reference should be had to the Figure in which absorbance is plotted against total quantity of effluent in millimeters. The principal fractions produced are characterized by the major peaks identified as "Wash," "A", and "BC" (or as "B" and "C" fractions).

By using specific antisera to each of the fractions studied mycobacterial organisms and testing these in immunodiffusion against each chromatographic fraction, it was possible to enumerate the number of antigens in each fraction and characterize each antigen as to its specificity for the M. tb. group or for cross-reactivity with atypical mycobacteria.

Viewing the FIGURE, as an example, it will be seen that antigens in the RIRV culture filtrate were identified in that particular experiment. The antigens indicated by the dashed line having vertical white spaces are those common to one or more mycobacteria outside the M. tb. group. These bear the numbers 1, 3, 4, 6, 9, 10, 13, 14, 15, 20. In viewing the Wash Fraction it is seen that antigens 1–4 are present; of these antigens only number 2 is identified as being specific to the *M. tb.* group. Broadly, the next step is to sub-fractionate or remove and separate the cross-reactive antigens from the *M. tb.* specific antigens in a fraction and then prepare the new test substance from the sub-fractions containing only *M. tb.* specific antigens. It should be mentioned that filtrates and chromatographic fractions vary when repeating studies on any one organism. For instance, RIRV filtrate does not always contain exactly 20 antigens and the Wash Fraction may contain more than 4 with at least one being specific to *M. tb.*

In accordance with the present development, in recent experiments conducted substantially as in the previous example, the Wash Fraction from several *M. tb.* organisms was subjected to discontinuous disc electrophoresis to separate the antigens therein. Disc electrophoresis, as used herein, basically comprises passing a culture filtrate, or as in this case a fraction thereof, through a column consisting of three stacked polyacrylamide gel zones each having a different gel concentration. In these tests the upper zone was 5.0% polyarylamide, the middle 7.0% and the lower 10.5%. In order to isolate and characterize materials separated by electrophoresis, the gel columns were sliced into numerous "discs"; each was immersed in a suitable liquid so as to elute the antigen from the gel. After centrifugation, the gels were discarded and the supernatant fluid containing soluble antigens tested. In one experiment, using a H37Rv Wash Fraction one *M. tb.* specific antigen identified as 10-10 was found to be retained in the 10.5 disc. On another occasion using a C-3 Wash fraction, an antigen identified as 8-10 was also retained at the same location in the 10.5% disc zone, as was the case with the 10-10 antigen of H37Rv. These two antigens were found to be identical when later tested by immunodiffusion.

The chromatographic A fraction from *M. tb.* (human) organisms was also subjected to separation. This was accomplished by means of disc electrophoresis as described above. However, in order to explain yet another method, subfractionation by use of isoelectric focusing also was accomplished and will be described. Briefly, isoelectric focusing is performed in a column having a plurality of horizontally aligned sugar solutions of varying sugar concentration. The column is provided with means at the upper end to maintain a low pH or high pH and means at the lower end to maintain the opposite. Electrical connections to the top and bottom of the column are also provided. The fraction to be studied is mixed with a carrier, which is identified as Ampholine, a proprietary reagent sold by LKB Industries, Inc. The Ampholine and sample are then loaded into a center position in the column. When electrical power is applied, the Ampholine constituant components will move upwardly or downwardly to stabilize at a level where a particular pH is established. Individual components in the sample are carried to a particular zone where they too stabilize, i.e., are said to be focused. A second focusing over a narrow pH range can be effected so as to permit a further separation.

An A fraction of concentrated culture filtrate of C-3 tubercle bacillus (as identified above) was obtained by DEAE cellulose chromatography, analysed and found to contain 7 antigens by immunodiffusion. This fraction was concentrated and subjected to isoelectric focusing over a pH range of 3 to 5, using 4% Ampholine concentration. After 48 hours at 600 volts, the column was eluted and the eluate collected in a series of successive tubes. Tubes identified as 11 thru 20 were pooled and contained material that focused between pH 3.70 and 4.12.

These pooled ten tubes were subjected to a second isoelectric focusing and the ampholyte contained therein established a linear gradient over the pH range of 3.10 to 4.15. By immunological testing antigens were found in two separate regions. In the first region with an isoelectric pH range of 3.2 to 3.7, there were two antigens, both of which were specific for all strains of human and bovine tubercule bacilli tested. (The antigens did not react with antisera to any of the atypical mycobacteria). These two specific antigens were contained in a fraction identified as 11-22B. The other two antigens had isoelectric points above 4.0 and were cross-reactive with one or more of the atypical organisms. When another contiguous ten tubes from the 4% Ampholine procedure were refocused in a similar manner, another *M. tb.* specific antigen and two cross-reactive antigens were eluted together.

The B and C peaks have been subfractionated by disc electrophoresis as above to accomplish separation of antigens.

Antigens from various culture filtrates were separated by combinations of the processes outlined above and were tested in guinea pigs as set forth hereinafter.

SKIN TESTING

In a first battery of tests guinea pigs which had been infected by one or more mycobacteria were employed to determine skin delayed hypersensitivity reactions to certain fractions. Groups of six pigs were infected singly or multipally by mycobacteria as listed below:

1. H37 RV - identified herein before.
2. Group I - atypical, M. Kansasii.
3. Group II - atypical mycobacterium, Gause strain.
4. Group III - atypical mycobacteria of the Avian and Battey types.
5. Group IV - atypical, M. fortuitum.

Some pigs had multiple infections and these are listed in their order of infection in Table I.

Table I

| Pig Group | Infecting Mycobacteria H37RV | Group I | Group II | Group III | Group IV |
|---|---|---|---|---|---|
| Batch I | only | | | | |

Table I-continued

| Pig Group | H37RV | Infecting Mycobacteria Group I | Group II | Group III | Group IV |
|---|---|---|---|---|---|
| Batch II | second and final | | | | first |
| Batch III | third and final | second | first | | |
| Batch IV | third and final | | | first and second | |
| Batch V | third and final | | first | second | |

Certain isoelectric focused subfractions prepared from the A fractions of ion-exchange chromatography were selected for delayed hypersensitivity skin testing in the pigs listed hereinbefore:

Table II

| Tubercule Bacilli | Subfraction | Antigens (by immunodiffusion) |
|---|---|---|
| C-27 | 4-7A | 2 M.tb. specific |
| C-3 | 11-22B | 2 M.tb. specific |
| H-37RV | 1-3B | 3 crossreactive with atypical mycobacteria |
| C-3 | 2-4B | 3 crossreactive with atypical mycobacteria |

Comparative tests were run in which the pigs from each Batch of Table I were inoculated with each of the subfractions of Table II. As a control, the pigs were inoculated also with purified protein derivative (P.P.D.), a crude tuberculin. All dosages were at 0.0001 mg. (protein) which is the standard "intermediate" P.P.D. dose. The pigs were examined at 48 and 78 hours to determine whether any skin reaction took place; if so, the size or diameter of the induration was measured and reported in millimeters.

Table III

| Pigs | Average Skin Induration for the Inoculant | | | | |
|---|---|---|---|---|---|
| | PPD | 4-7A | 11-22B | 1-3B | 2-4B |
| Batch I | 7-15mm | N.R.* | NR | 11-mm | 8-17mm |
| Batch II | 14 mm | N.R. | NR | NR | 14 mm |
| Batch III | 13 mm | NR | NR | 5 mm | 12 mm |
| Batch IV | 14 mm | NR | NR | NR | NR |
| Batch V | 10 mm | NR | NR | NR | NR |

*No reaction

From these tests, it can be seen that the fractions (4-7A and 11-22B) containing specific antigens did not cause a reaction in the infected pigs, even though they had reacted with antisera in vitro (see Table II), while the tests do show that cross-reactive antigens apparently give similar reaction as use of P.P.D. These particular cross-reactive antigens may be more potent, than the ones that did not cause a reaction, or there may have been more antigens present when reaction was effected than when there was no reaction. It is noteworthy that earlier infections with atypical mycobacteria, such as Group III organisms, negated the responsiveness of pigs subsequently infected with M. tb. to the purified cross-reactive fractions and not to the crude P.P.D. (see Batches II, IV, and V).

Additional tests were then run using the subfractions identified in Table IV for the purpose of determining what, if any, effect an increased dosage would have.

Table IV

| Tubercule Bacilli | Fraction | Antigen |
|---|---|---|
| C-3 (See Table II) | 11-22B | 2 M.tb. specific |
| TMC-107 | 14-31B | 1 M.tb. specific |
| C-3 | 11-20Z | 4 M.tb. specific |
| | 11-20A | |

All fractions identified in Table IV were prepared by chromatographic separation of culture filtrate and isoelectric focusing of the chromatographic A fraction.

Tests using these fractions were run on pigs infected with M. tb. human (H37RV), M. tb. bovine strains, and three atypical mycobacterial strains. The injected dose of each antigen was 0.001 mg., a dosage ten times greater than the usual PPD dosage. No reactions occurred in pigs infected with atypical mycobacteria. At these dosage levels the 14-31B fraction reacted positively in 3 out of 5 animals (human strain only); and the 11-20Z fraction reacted in 4 out of 5 animals (human) and 2 of 5 bovine strain animals. The 11-22B and 11-20A fractions did not react at all. (It will be recalled that in the previous tests at 0.0001 mg. dosages the 11-22B fraction did not react at all to animals sensitized to H37RV).

Although tests with some M. tb. specific antigens were positive, the increased dosage did not result in an acceptable degree of delayed hypersensitivity response.

Additional tests were run with these and other fractions containing M. tb. specific antigens to determine whether even greater increments of dosage would produce satisfactory skin reaction. These additional fractions are identified as follows:

Table V

| Tubercule Bacilli | Fraction | Antigen |
|---|---|---|
| H37RV | 1-3A | 2-3 M.tb. specific |
| C-3 | 8-10 | 1 M.tb. specific |
| H37RV | 10-10 | 1 M.tb. specific |

The 8-10 antigen is isolated by discontinuous gel electrophoretic separation of the Wash Fraction, in which the specific antigen was found in the 10.5% gel disc. The 10-10 fraction is prepared in the same manner as the 8-10 fraction.

Guinea pigs infected only with the RIRV strain of M. tb. were used in these additional tests to determine the effect of dosage for single antigens or fractions. Table VI hereinafter sets forth the results of these tests, and as in previous tables, compares the test antigens to a reference dose of PPD. Except for PPD, the dosages used were 0.01, 0.001 and/or 0.0001 milligrams. The size of the indurations in millimeters were measured as to length, width and height.

Table VI

| Pigs | PPD | 11–22B | 4–7A | 11–20Z | | | 14–31B | | 1–3A | | | 8–10 | | | 10–10 | | |
|---|---|---|---|---|---|---|---|---|---|---|---|---|---|---|---|---|---|
| | Dosage in milligrams (protein) | | | | | | | | | | | | | | | | |
| | 0.0001 | 0.01 | 0.01 | 0.01 | 0.001 | 0.0001 | 0.01 | 0.001 | 0.01 | 0.001 | 0.0001 | .01 | .001 | .0001 | .01 | .001 | .0001 |
| 1 | 14× 15× 1 16× | NR | NR 5× | NR | NR | NR | NR | NR | 4× 4× 0.5 | NR | NR | NR 9× | NR | NR | NR | NR | NR |

Table VI-continued

| Pigs | PPD | Dosage in milligrams (protein) 11-22B | 4-7A | | 11-20Z | | | 14-31B | | 1-3A | | | 8-10 | | | 10-10 | |
|---|---|---|---|---|---|---|---|---|---|---|---|---|---|---|---|---|---|
| 2 | 18× 3.5 | NR | 5× 0.5 | NR | NR | NR | — | NR | — | NR | NR | 8× 1 | NR | NR | NR | NR | NR |
| 3 | 13× 13× 1 | — | — | — | NR | NR | — | NR | — | NR | NR | — | NR | NR | — | NR | NR |
| 4 | 11× 12× 1 | — | — | — | NR | NR | — | NR | — | NR | NR | — | NR | NR | — | NR | NR |
| 5 | 16× 13× 2 | — | — | — | 15×14 ×2 | NR | — | NR | P | 13× 11× 0.5 | 8× 8× 1× | P | 8× 8× 1× | NR | — | NR | NR |

NR - no reaction
P - presumed positive reaction, because ten times lower dose was positive
— - not tested It should be noted that a concentration of 0.01 mg. (protein) is 100 times the normal PPD dosage. Even at these high dosage levels there were only 5 positive responses by purified antigens out of 14 tests at a dose of 0.01 mg. However, it is also seen that greatly increased dosages do evoke a positive response, when lower doses don't.

In order to determine the effect of mixed subfractions or a plurality of antigens, three mixtures were prepared each containing equal amounts of 3 subfractions as set forth below:

| | | | | | |
|---|---|---|---|---|---|
| Mixture I | 11-22B | + | 10-10 | + | 8-10 |
| Mixture II | 11-22B | + | 10-10 | + | 11-20Z |
| Mixture III | 4-7A | + | 10-10 | + | 11-20Z |

The three mixtures were prepared so that each dose would contain 0.002 mg. protein which is about 20 times greater than that of the PPD standard dosage. (Each component of each mixture therefore had a concentration of about 0.0007 mg.). The doses each in a volume of 0.1 ml. were injected into guinea pigs which were previously infected with the RIRV strain of *M. tb.* As in the other tests, PPD control inoculations were made in addition to injections of the mixes. The test results are summarized in Table VII, skin induration expressed in millimeters, as before.

Table VII

| Pig | PPD | Mix I | 8-10 | Mix II | 11-22B | Mix III | 4-7A |
|---|---|---|---|---|---|---|---|
| | .0001mg | .002mg | .002mg | .002mg | .002mg | .002mg | .002mg |
| 1 | 12×15×2 | NR | NR | 10×7×1 | 10×8×1 | 13×11×1 | 6×6×0.5 |
| 2 | 15×15×2 | NR | NR | 12×12×0.5 | 5×5×0 | 13×13×1 | NR |
| 3 | 7×5×1 | NR | NR | 12×10×0.5 | NR | — | — |
| 4 | 17×16×2 | 5×4×0.5 | 5×5×0.5 | 12×13×1.5 | 10×10×10 | — | — |
| 5 | 10×11×2 | 8×8×1 | 5×5×0.5 | 22×21×3 | 16×14×2 | — | — |

The reactions produced by Mix II, which contains a total of at least 5 different *M. tb.* specific antigens, are clearly very similar to the results produced by PPD. When compared to the reaction produced by the 11-22B subfraction alone (see Table VI) it is clear that the mixture produced some synergistic result. This is based upon the observation that in the tests tabulated in Table VI fraction 10-10 did not react at all and 11-20Z reacted in only one of five animals, at a dose of 0.001 mg. Thus, the reactions produced by mixture 11 are greater, i.e., synergistially enhanced, over the results to be expected by the 11-22B or any single component alone. Similar synergistic results are noted with Mix III as compared to one of its components, fraction 4-7A.

These tests clearly indicate that tuberculins which are free of cross-reactive antigens and include a plurality of *M. tb.* specific antigens can yield reactions which are equivalent to those produced by PPD.

It will be appreciated that once the subfractions are obtained which contain *M. tb.* specific antigens and are free of cross-reactive antigens, other combinations may be derived for use as skin testing materials. For example, it has been found that a single *M. tb.* specific antigen can be isolated in the 10.5% gel zone, employing the discontinuous gel electrophoretic technique for each of the Wash, A and BC chromatographic fractions of H37RV or C3 culture filtrates. A mixture of three such *M. tb.* specific antigens, each possessing clearly different physicochemical characteristics, may be expected to prove to be a more broadly reactive mixture than the combination of three *M. tb.* specific antigens derived from the same chromatographic fraction, all closely related chemically. It is likely that the "ideal" tuberculin, that causes unquestionably positive delayed hypersensitivity reaction only in *M. tb.* sensitized individuals, at a protein dose in a range comparable to that of current crude tuberculins, will be a mixture of three or more *M. tb.* specific antigens derived from two or more chromatographic fractions and possibly from more than one *M. tb.* organisms.

What I claim as new and desire to secure by Letters Patent of the United States is:

1. In a method for preparing a test substance having both high specificity and high sensitivity for detecting immunological sensitization to *M. tb.* in humans and animals which includes the steps of:

a. providing at least one *M. tb.* culture filtrate; and b. fractionating said filtrate by means of ion-exchange chromatography so as to produce a plurality of chromatographic fractions;

the improvement which comprises:

c. subfractionating a plurality of said chromatographic fractions so as to produce a plurality of subfractins, each of which contains at least one *M. tb.* specific antigen and is substantially free of cross-reactive antigens; and d. mixing a plurality of said *M. tb.* specific subfractions so as to produce a test substance which is substantially free of cross-reactive antigens and contains a plurality of *M. tb.* specific antigens.

2. The method claimed in claim 1 wherein at least one chromatographic fraction is subfractionated by means of polyacrylamide gel electrophoresis.

3. The method claimed in claim 1 wherein at least one chromatographic fraction is subfractionated by means of isoelectric focusing.

4. The method claimed in claim 1 wherein at least one chromatographic fraction is subfractionated by isoelectric focusing and polyacrylamide gel electrophoresis.

5. The material made by the method of claim 1.

6. The material made by the method of claim 2 wherein the process of gel electrophoresis utilizes three stacked discs of polyacrylamide gels having concentrations of 5%, 7% and 10.5%, and wherein at least one *M. tb.* specific subfraction is obtained from the 10.5% gel from each of a plurality of chromatographic fractions.

7. The material made by the method of claim 1 wherein at least two *M. tb.* specific subfractions are from the same chromatographic fraction.

8. In an antigenic test substance prepared from at least one *M. tb.* culture filtrate for detecting immunological sensitization to *M. tb.*, in humans and animals, the improvement which comprises providing a substance having both high specificity and high sensitivity, which test substance is substantially free of cross-reactive antigens and consists essentially of a plurality of *M. tb.* specific antigens at least one of which is selected from each of at least two major groups wherein:

Group I consists of the *M. tb.* specific antigens present in the Wash fraction of said filtrate which is obtained by DEAE ion-exchange chromatography;

Group II consists of the *M. tb.* specific antigens present in the A fraction of said filtrate or extract which is obtained by DEAE ion-exchange chromatography; and Group III consists of the *M. tb.* specific antigens present in a BC fraction of said filtrate or extract which is obtained by DEAE ion-exchange chromatography.

* * * * *